US011479819B2

(12) United States Patent
Ramani

(10) Patent No.: US 11,479,819 B2
(45) Date of Patent: Oct. 25, 2022

(54) NON-INVASIVE METHOD FOR MONITORING TRANSPLANTED ORGAN STATUS IN ORGAN-TRANSPLANT RECIPIENTS

(71) Applicant: ACRANNOLIFE GENOMICS PVT. LTD., Chennai (IN)

(72) Inventor: Avinash Ramani, Chennai (IN)

(73) Assignee: ACRANNOLIFE GENOMICS PVT. LTD., Chennai (IN)

( * ) Notice: Subject to any disclaimer, the term of this patent is extended or adjusted under 35 U.S.C. 154(b) by 0 days.

(21) Appl. No.: 16/772,546

(22) PCT Filed: Dec. 14, 2018

(86) PCT No.: PCT/IN2018/050838
§ 371 (c)(1),
(2) Date: Jun. 12, 2020

(87) PCT Pub. No.: WO2019/116393
PCT Pub. Date: Jun. 20, 2019

(65) Prior Publication Data
US 2020/0385809 A1    Dec. 10, 2020

(30) Foreign Application Priority Data
Dec. 15, 2017 (IN) .............................. 201741040813

(51) Int. Cl.
*C12Q 1/6883* (2018.01)
(52) U.S. Cl.
CPC ...... *C12Q 1/6883* (2013.01); *C12Q 2600/112* (2013.01); *C12Q 2600/156* (2013.01)
(58) Field of Classification Search
None
See application file for complete search history.

(56) References Cited

U.S. PATENT DOCUMENTS

| | | | |
|---|---|---|---|
| 2015/0086477 A1 | 3/2015 | Mitchell et al. | |
| 2016/0145682 A1* | 5/2016 | Woodward | C12Q 1/6876 506/4 |
| 2019/0203285 A1 | 7/2019 | Lee et al. | |

FOREIGN PATENT DOCUMENTS

| WO | 2011057061 A1 | 5/2011 |
| WO | 2014194113 A2 | 12/2014 |
| WO | 2016167408 A1 | 10/2016 |
| WO | 2016176662 A1 | 11/2016 |

OTHER PUBLICATIONS

Beck et al., (2013) Digital droplet PCR for rapid quantification of donor DNA in the circulation of transplant recipients as a potential universal biomarker of graft injury. Clin Chem 59(12): 1732-1741 (10 pages).
Gielis et al., (2015) Cell-Free DNA: An Upcoming Biomarker in Transplantation. Am J Transplant 15(10): 2541-2551 (11 pages).
Supplementary European search report and opinion for European application No. 18887915.9; dated Jul. 15, 2021. 11 pages.
Pakstis et al., "SNPs for Individual Identification", Science Direct, Genetic Supplement, 2008, pp. 479-481, Elsevier Ireland Ltd. (3 pages).
Adamek et al., "A fast and simple method for detecting and quantifying donor-derived cell-free DNA in sera of solid organ transplant recipients as a biomarker for graft function", Clinical Chemistry and Laboratory Medicine (CCLM). Jul. 1, 2016, pp. 1147-1155, vol. 54(7). (9 pages).
Beck et al., "Digital Droplet PCR for rapid quantification of donor DNA in the Circulation of transplant recipients as a potential universal biomarker of Graft Injury" Clinical chemistry, 2013, pp. 1732-1741, vol. 59(12). (11 pages).
Beck et al., "Donor-derived cell-free DNA is a novel universal biomarker for allograft rejection in solid organ transplantation" Transplantation Proceedings, Oct. 1, 2015, pp. 2400-2403,vol. 47(8), Elsevier Inc, New York. (4 pages).
Breitbach et al., "Direct Quantification of Cell-Free, Circulating DNA from Unpurified Plasma", PLOS One, Mar. 2014, pp. 1-11, vol. 9(3), e87838. (11 pages).
Bromberg et al., (2017) Biological Variation of Donor-Derived Cell-Free DNA in Renal Transplant Recipients: Clinical Implications. The Journal of Applied Laboratory Medicine 2(3): 309-321. (13 pages).
Crespo-Leiro et al., Noninvasive monitoring of acute and chronic rejection in heart transplantation. Current Opinion in Cardiology, May 1, 2017, pp. 308-315, vol. 32(3). (8 pages).
De Vlaminck et al., "Circulating cell-free DNA enables noninvasive diagnosis of heart transplant rejection", Science Translational Medicine, 2014, pp. 241-277, vol. 6(241). (19 pages).
De Vlaminck et al. "Noninvasive monitoring of infection and rejection after lung transplantation", Proceedings of the National Academy of Sciences. Oct. 27, 2015; pp. 13336-13341, vol. 112(43). (6 pages).
Deng, The AlloMap™ genomic biomarker story: 10 years after. Clinical Transplantation. Mar. 2017; pp. 1-9, 31(3), e12900. (9 pages).
Gielis et al., "Cell-Free DNA: An Upcoming Biomarker in Transplantation", American Journal of Transplantation, 2015, pp. 2541-2551, vol. 15, Wiley Periodicals Inc. (11 pages).
Grskovic et al., Donor-derived cell-free DNA in plasma increases with rejection and decreases after treatment in kidney transplant recipients. J Am Soc Nephrol, 2015, 26:1143 (1 page).

(Continued)

*Primary Examiner* — Carla J Myers
(74) *Attorney, Agent, or Firm* — Roach Brown McCarthy & Gruber, P.C.; Kevin D. McCarthy

(57) ABSTRACT

The present invention pertains to a non-invasive method for monitoring transplanted organ status in organ-transplant recipients by determining the ratio of donor derived marker sequences to the marker sequences of the transplant recipient from circulating cell free DNA of the transplant recipients using digital droplet PCR. The invention also determined a normalized threshold value of the total circulating cell free nucleic acids healthy as well as in post-transplantation patients for assessing and monitoring transplanted organ status in organ-transplant recipients.

9 Claims, 2 Drawing Sheets

Specification includes a Sequence Listing.

(56) References Cited

OTHER PUBLICATIONS

Grskovic et al., "Validation of a clinical-grade assay to measure donor-derived cell-free DNA in solid organ transplant recipients". The Journal of Molecular Diagnostics, Nov. 1, 2016, pp. 890-902, vol. 18(6). Elsevier Inc. (13 pages).

Huggett et al., "Digital PCR as a novel technology and its potential implications for molecular diagnostics", Clinical Chemistry, 2013, pp. 1691-1693, vol. 59(12). (3 pages).

Kobashigawa et al., Increased plasma levels of cell-free DNA correlate with rejection in heart transplant recipients. The Journal of Heart and Lung Transplantation, Apr. 1, 2014, pp. S14, vol. 33(4). (1 page).

Lee et al., Evaluation of digital PCR as a technique for monitoring acute rejection in kidney transplantation. Genomics & Informatics, 2017, pp. 2-10, vol. 15(1). (9 pages).

Macher et al., "Monitoring of transplanted liver health by quantification of organ-specific genomic marker in circulating DNA from receptor", PLOSOne, 2014, pp. 1-18, vol. 9(12):e113987. (18 pages).

Oellerich et al., Graft-derived cell-free DNA as a marker of graft integrity after transplantation. Chapter 7 in Personalized Immunosuppression in Transplantation, 2016, pp. 153-176. (24 pages).

Oellerich et al., Graft-derived cell-free DNA as a marker of transplant graft injury. Therapeutic Drug Monitoring, 2016, S75-79, vol. 38 (2S). (5 pages).

Schütz et al., Graft-derived cell-free DNA, a noninvasive early rejection and graft damage marker in liver transplantation: A prospective, observational, multicenter cohort study. PLOS medicine, 2017, pp. 1-20, vol. 14(4): e1002286. (19 pages).

Sigdel et al., "A rapid noninvasive assay for the detection of renal transplant injury", Transplantation, 2013, pp. 97-101, 96(1). (10 pages).

Roedder et al., "Biomarkers in solid organ transplantation: establishing personalized transplantation medicine", Genome Medicine, 2011, pp. 1-12, vol. 3 (37). (12 pages).

Hoffmann et al., "Donor genomics influence graft events: The effect of donor polymorphisms on acute rejection and chronic allograft nephropathy", Kidney International, 2004, pp. 1686-1693, vol. 66. (8 pages).

Snyder et al., "Universal non-invasive detection of Solid-organ transplant rejection", PNAS, Apr. 2011, pp. 6229-6234, vol. 108(15). (6 pages).

Gadi et al., "Soluble Donor DNA Concentrations in Recipient Serum Correlate with Pancreas-Kidney Rejection", Clinical Chemistry, 2006, pp. 379-382, 52(3). (4 pages).

* cited by examiner

NON-INVASIVE METHOD FOR MONITORING TRANSPLANTED ORGAN STATUS IN ORGAN-TRANSPLANT RECIPIENTS

SEQUENCE LISTING

This application contains a sequence listing filed in electronic form as an ASCII.txt file entitled "KNS-002-US-Seqlisting-txt.txt" created on Dec. 14, 2018; and the size is 28 KB. The content of the sequence listing is incorporated herein in its entirety.

FIELD OF INVENTION

The invention pertains to the field of medical diagnostics with special reference to non-invasive method for monitoring transplanted organ status in organ-transplant recipients.

BACKGROUND

Transplantation is a life-extending medical procedure and the most preferred treatment option for end-stage organ damages as long-term mortality is almost 68-70% lower in patients receiving an organ-transplant than those patients who did not receive a transplant. Frequent monitoring of a transplanted graft is difficult as it requires highly invasive procedures like tissue-biopsy, regarded as the "Golden Standard" for determining rejection status of transplant graft and confirmation of graft-rejection, the method is highly invasive necessitating expensive hospitalization, and also carries significant medical risks, including internal bleeding and biopsy-induced transplant graft rejection. An accurate and timely diagnosis of organ transplant rejection in an organ transplant recipient is essential for survival of the organ transplant recipient. Also, the conventional method for detection of rejection is difficult, expensive, and risky, and do not have adequate specificity and sensitivity to elucidate the rejection status of a transplanted organ. In addition, this method suffers from many problems including high costs, variability in tissue biopsy between physicians, and severe patient discomfort.

Medical management of transplantation is one of the most challenging and complex specialities in modern medicine. Not all transplanted organ survives in the new body of a transplant recipient and thus, in a few cases, the organ gets rejected by the transplant-recipient, thereby creating critical, life-threatening medical emergency conditions. The important challenge for medical management in transplants is the management of graft-rejection that occurs mostly due to immunological response of the recipient's body against the transplanted organ. The hyper-acute transplant failure or hyper-acute transplant rejection caused due to rapid immunological response, accounts for a medical emergency and it is imperative to immediately remove the transplanted organ or tissue from the recipient or the acceptor. However, several precautionary measures are incorporated in the standard operating protocol (SOP) for transplants to minimize the chances of hyper-acute transplant rejection, or transplant failure that includes serotyping and 1-ILA cross-match, in order to determine the most appropriate donor-recipient/acceptor match and the use of combination of immunosuppressant drugs post-transplant.

In order to overcome several such limitations, with significant advancements in the area of genomics, non-invasive methods have been used, such as a method for measuring gene expression signals which tend to increase when organ transplant rejection occurs, a method for measuring the level of immune proteins, and the like. However, these methods also pose limitations as they tend to produce high false positive results due to the complex cross-reactivity of various immune responses and are based on tissue-specific gene expression signals. With the identification of donor-derived cell free-DNA (ddcfDNA) in the urine and blood of organ transplant recipients, methods have been proposed for non-invasive diagnosis of organ transplant rejection. However, the ddcfDNA is present in minute quantity, whereas the background DNA is present in abundance and poses a limitation to be used as a tool. Thus, a highly specific and sensitive method for analysing this ddcfDNA is required.

The present invention resolves the problems and risks of conventional tissue-biopsy method and the method is highly sensitive and specific for diagnosis of the status of a transplanted organ based on presence of the said one or more circulating nucleic acids markers.

OBJECT OF THE INVENTION

It is an object of the present invention to provide a non-invasive method for monitoring status of the transplanted organ in organ-transplant recipients by determining the ratio of donor derived markers sequences to the marker sequences of the transplant recipients from circulating cell free DNA of the transplant recipients.

Another object of the invention is to determine a normalized threshold value of the total circulating cell free DNA in healthy and clinically stable and post transplantation patients.

Another object of the invention is the profiling of the nucleic acids of the donor and the recipients and identification of markers.

DRAWINGS

DETAILED DESCRIPTION

Figure 1:
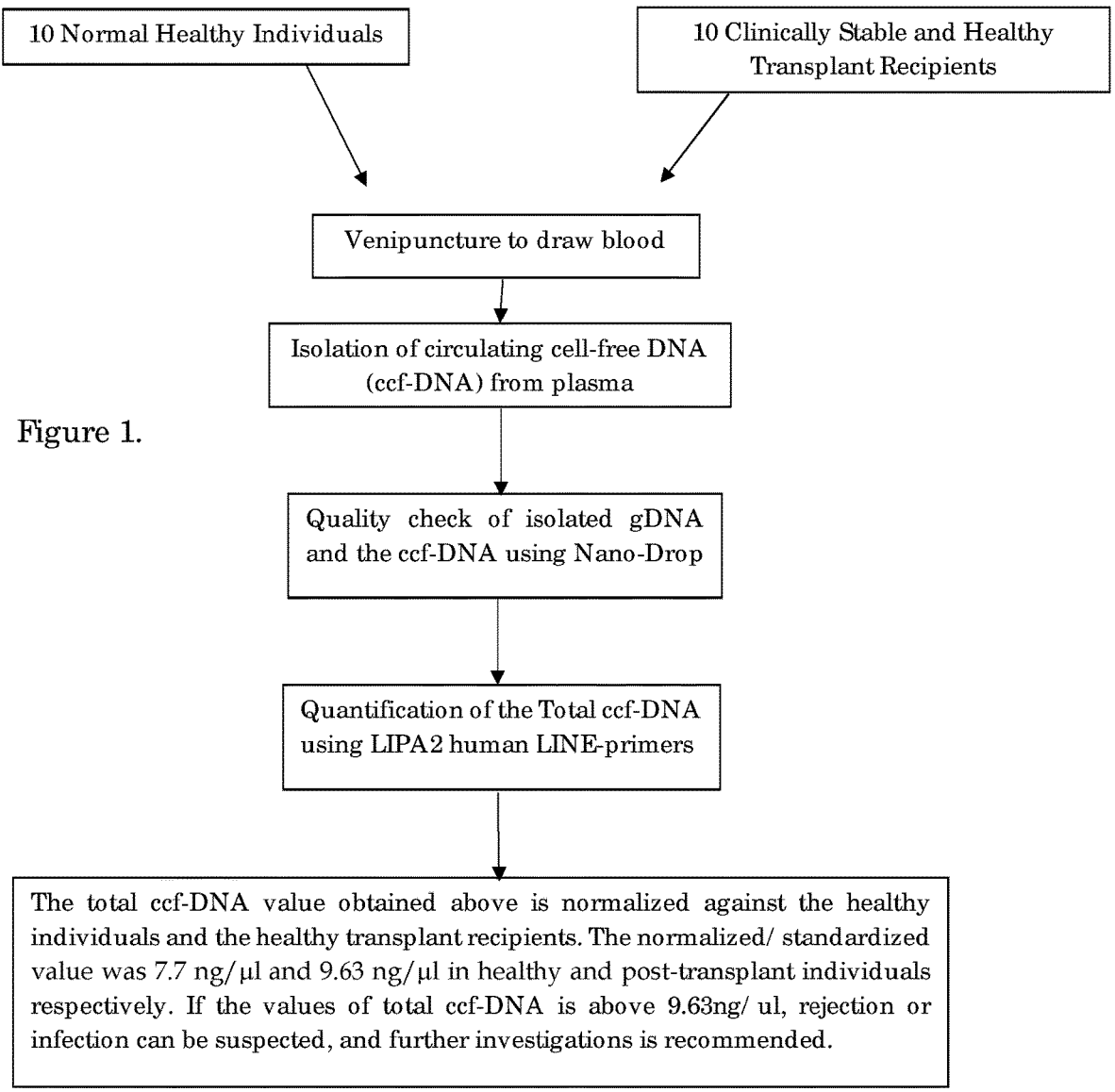
FIG. 1 is a flow chart which depicts the steps of the invention for monitoring the status with the total ccfDNA of the transplant recipients.
Figure 2:
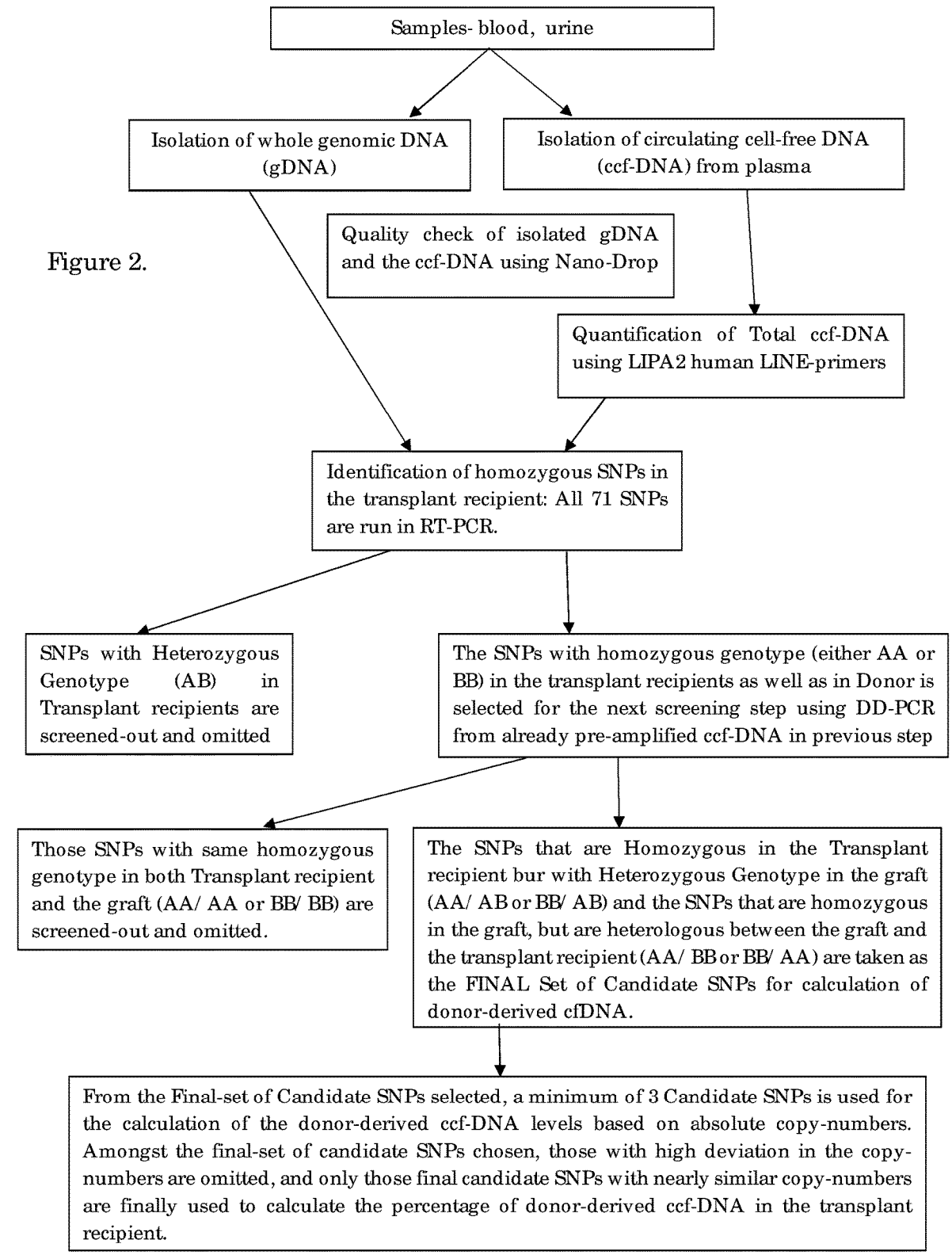
FIG. 2 is a flow chart which depicts the steps of the invention for monitoring the status with the donor-derived ccfDNA in the transplant recipients.

Accordingly, the present invention provides a non-invasive method for monitoring transplanted organ status in organ-transplant recipients by determining the ratio of donor derived marker sequences to the marker sequences of the transplant recipients from circulating cell free DNA of the transplant recipients using digital droplet PCR.

In one embodiment a normalized threshold value of the total circulating cell free nucleic acids of healthy as well as in post-transplantation patients is determined.

In addition, profiling of the nucleic acids of the donor and the recipients is performed for identification of markers.

The invention provides a method of monitoring the status of a transplanted organ in the transplant recipients, comprising of: (i) collection of sample from a subject who has received an organ transplant from a donor; (ii) identification of the marker sequences from the transplant recipients, wherein one or more nucleic acids that are derived from the donor are identified based on a predetermined profile of markers; and (iii) identification of said one or more marker sequences by analysing the circulating cell free nucleic acids from the transplant recipients by digital droplet polymerase chain reaction (DDPCR); (iv) arriving at a ratio of the donor derived marker sequences to the recipient-derived marker sequences expressed in terms of percent; (v) assessment of the organ status of the transplant recipients on comparison calculated percent with the cut off value.

The cut off value which is the ratio of the donor derived ccfDNA marker sequences to the recipient-derived marker sequences is calculated and expressed as percentage.

The cut off value for monitoring the status of the transplanted organ of the transplant recipient varies with the transplant type; wherein the value is in the range of 0.1% to 2.75% in heart transplant recipients; <15% in liver transplant recipients and 0.3% to 3.5% in kidney transplant recipients; wherein the ratio of the donor derived marker sequences to the recipient-derived marker is greater than the cut off value, the recipients organ is considered as in organ rejection state; wherein the ratio of the donor derived marker sequences to the recipient-derived marker is lesser than the cut off value, the recipient organ status is considered as healthy.

The invention provides a method of monitoring the status of a transplanted organ in the transplant recipients, comprising of: (i) collection of sample from a subject who has received an organ transplant from a donor; (ii) quantification of the total circulating cell free DNA in healthy subjects and post transplantation patients; (iii) arriving at a normalised value of the total circulating cell free DNA in healthy subjects and post transplantation patients; (iv) assessment of the organ status of the transplant recipients by comparing the normalised threshold value of total circulating cell free nucleic acids.

A normalized threshold value of the total circulating cell free nucleic acids in a healthy subject is <7.7 ng/μl and <9.63 ng/μl in clinically stable and healthy post-transplantation patients.

The normalized threshold value of the total circulating cell free DNA in transplant recipients if greater than 9.63 ng/μl, the recipient is considered as in organ rejection state; and wherein the value of the circulating cell free DNA in the transplant recipient is less than or equal to 9.63 ng/μl, the recipient organ status is considered as healthy.

The organ-transplant status comprises of graft-rejection, intolerance, allograft injury not amounting to rejection, tolerant healthy transplant function, transplant survival, chronic transplant injury, or pharmacological immunosuppression, all of which is determined by the said non-invasive method. The allograft injury that may not be a rejection, can be ischemic injury, any viral or other pathogenic infections, a reperfusion injury, peri-operative ischemia, chronic hypertension, physiological stress, injuries caused by pharmaceutical agents and injuries due to reactive oxygen species.

The biological sample is selected from whole blood, plasma, serum, saliva or urine.

The marker sequence is a polymorphic genomic marker and is selected from one or more single nucleotide polymorphisms (SNP's), restriction fragment length polymorphisms (RFLP's), short tandem repeats (STRs), variable number tandem repeats (VNTR's), hypervariable regions, mini satellites, microsatellites, dinucleotide repeats, trinucleotide repeats, tetranucleotide repeats, simple sequence repeats, or insertion or deletion polymorphisms.

The preferred polymorphic marker sequences comprises of one or more of SNPs.

The method comprises of genotyping the transplant recipient to determine the donor-derived marker in the transplant recipients. The method further comprises profiling of markers, wherein the donor-derived markers in the transplant recipients is clearly distinguishable.

The transplant can be an organ transplant or a skin/tissue transplant.

The organ transplant is selected from one of kidney transplant, heart transplant, liver transplant, pancreas transplant, lungs transplant, intestine transplant, bone marrow or thymus transplant or a combination of more than one organ transplant.

The marker sequences can be derived from one of circulating cell free DNA, which comprises of double-stranded DNA, or single-stranded DNA, single-stranded DNA hairpins, and DNA/RNA. The nucleic acid can be mRNA also.

The amplified marker sequences of total ccfDNA is analysed for the donor-derived marker sequences in the transplant recipients using DDPCR, The method is cost-effective, rapid and absolute quantification of nucleic acids by counting molecules and also have superior analytical precision compared to conventional PCR or qPCR based detection methods or next generation (NGS) sequencing. The method described herein with the analysis of amplified marker sequences of the donor derived circulating cell free nucleic acid with DDPCR has a specificity between 90% and 100%.

The markers were selected to differentiate the donor-derived ccfDNA from the total ccfDNA in the transplant recipients. The markers of the invention was selected in such way that it represents sequences spanning the entire human chromosome, including the X and Y chromosomes. The SNP markers selected are those with high minor allele frequency ([MAF>40] or MAF>0.4000). For arriving at the candidate 71 SNPs with high Minor Allele Frequency (minor allele frequency [MAF>40] or MAF>0.4000) an extensive bioinformatics analysis was performed. Further, the SNPs are selected in such a way that it includes SNPs taken from genes that have been proven to play role in tissue rejection, and cellular necrosis ie, the SNPs with high MAF includes SNPs from those genes that are clinically proven to have a role in tissue rejection and necrosis. Furthermore, the SNPs also includes those SNPs that are proven to help differentiate between two individuals. The final SNPs selected were those having high MAF in both rejection-related genes as well as in the markers that are proven to differentiate between two unrelated individuals, and that spanning across all the chromosomes.

The donor derived ccfDNA amplification is performed by DDPCR for the identification of the organ transplant status in the transplant recipient. Firstly, screening of all the High-MAF SNPs was done in both genomic DNA as well as the circulating cell-free DNA using Real-Time PCR. In this step, the SNPs that have heterozygous genotype in the recipient are filtered out and eliminated, since they cannot be used for quantification in DDPCR. In the next step, the pre-amplified ccfDNA is used as the template, and the candidate SNPs are filtered out and the assay is set for the individual patient. The SNPs which are homozygous in the recipient and that could be either heterozygous or homozygous on the allele in the graft and is preferably heterologous between the recipient and the graft is chosen as the final candidate SNPs. This step is performed as a DDPCR assay.

All homozygous SNPs were subsequently used to genotype the recipient's ccfDNA enabling the measurement of the donor derived ccfDNA fraction by using a hydrolysis-based SNP assay in combination with DDPCR. The number of candidate SNPs obtained ranged between 2 and 9 with a minimum of 3 SNPs per patient in the above method. The average of the 3 SNPs determined is measured as absolute copy numbers (copies/µl) and can be expressed as percentage of donor-derived ccfDNA markers to the recipient derived markers.

The candidate marker sequences for monitoring the organ status are selected from the set of 71 SNPs with the rf numbers and their location in the chromosome with high Minor Allele Frequency (minor allele frequency [MAF>40] or [MAF>0.4000]) is as provided in Table 1. The primers for amplification of circulating cell free nucleic acid are provided in table 1.

TABLE 1

Set of markers of the invention:

| Sl. No. | rs IDs | Gene | Chr | MAF | Type | Forward primer | Reverse primer |
|---|---|---|---|---|---|---|---|
| 1 | rs2493132 | AGT | 1 | 0.4884 | SNP | AAAGACGCTGGGATTTGACA (SEQ. ID. NO: 1) | GTCTCCCTTCGAAAGAGAGC (SEQ. ID. NO: 2) |
| 2 | rs6667487 | RHOU | 1 | 0.4988 | SNP | TCATTGAAGTCAGGCTGTGC (SEQ. ID. NO: 3) | GGTGAGCAACTTGGAAGCTC (SEQ. ID. NO: 4) |
| 3 | rs553921764 | IL10 | 1 | 0.4982 | INDEL (Insertion/deletion), upstream variant | TCCTCACCCTACTGTACACC (SEQ. ID. NO: 5) | ACACAGGGAGGATGAGTGAT (SEQ. ID. NO: 6) |
| 4 | rs4233335 | KYAT3 | 1 | 0.4946 | SNP | ATTCTGGTCTCCGCTGTTTC (SEQ. ID. NO: 7) | GTGAACAGAACCTCAGGTCT (SEQ. ID. NO: 8) |
| 5 | rs10900556 | REN | 1 | 0.4425 | SNP | GTCTGGAATCATGGGCAAGT (SEQ. ID. NO: 9) | ACCTAGGGATGCTAAGGTT (SEQ. ID. NO: 10) |
| 6 | rs1449265 | ITGA4 | 2 | 0.4892 | SNP transcript variant | CTGAGAGGCACTCATGTGGA (SEQ. ID. NO: 11) | AAGAAGGAGGCAATGCAGAA (SEQ. ID. NO: 12) |
| 7 | rs7603052 | PDCD1 | 2 | 0.4692 | SNP | GAAAAGGGTTGAGCCTGTCA (SEQ. ID. NO: 13) | TCATCACGGGTACTGTGAGC (SEQ. ID. NO: 14) |
| 8 | rs1317808 | MSH2 | 2 | 0.4973 | SNP | GCCACCTTAGCCTCCCAAAG (SEQ. ID. NO: 15) | AGGGTGACTGTATTAATTATTGTTCAAACT (SEQ. ID. NO: 16) |
| 9 | rs2229813 | COL4A4 | 2 | 0.493 | SNP Missense Variant | TCCAGTCCTTTGTCTCCAGA (SEQ. ID. NO: 17) | AGTGCGGCCTGAAAGAAATA (SEQ. ID. NO: 18) |
| 10 | rs4851521 | IL1R2 | 2 | 0.493 | SNP | CACCCACAACTCTGCTGTAA (SEQ. ID. NO: 19) | GATGTTCTGGATCCCTCAGC (SEQ. ID. NO: 20) |
| 11 | rs7653603 | MED12L | 3 | 0.499 | SNP transcript variant | AGGGGAAAAAGTCAAAGGCA (SEQ. ID. NO: 21) | CCTTTCCCGAGTATGCACTT (SEQ. ID. NO: 22) |
| 12 | rs6791557 | TGFBR2 | 3 | 0.497 | SNP Missense Variant | GAAGATATGGGTTGGGTGCA (SEQ. ID. NO: 23) | GTCTTCCAACACCCATGCTA (SEQ. ID. NO: 24) |
| 13 | rs7652776 | CNTN4 | 3 | 0.4645 | SNP | GAGGGCTTTGGAGTGGAAAT (SEQ. ID. NO: 25) | TCCAAGGTTTGCTCAAGAGG (SEQ. ID. NO: 26) |
| 14 | rs9131 | CXCL2 | 4 | 0.4387 | SNP - 3'UTR Variant | CTGTTGTGCAGTCAGCTTTC (SEQ. ID. NO: 27) | CATACATTTCCCTGCCGTCA (SEQ. ID. NO: 28) |
| 15 | rs352007 | PF4 | 4 | 0.1931 | SNP | AGCAAATGCACACACGTAGG (SEQ. ID. NO: 29) | ATTTGCAAACCCAAGGACTG (SEQ. ID. NO: 30) |
| 16 | rs1818782 | DAB2 | 5 | 0.4974 | SNP | CCAAGCACAGGGTCTCATTT (SEQ. ID. NO: 31) | GAAACCCTTCTTCCCTCTGG (SEQ. ID. NO: 32) |

TABLE 1-continued

Set of markers of the invention:

| Sl. No. | rs IDs | Gene | Chr | MAF | Type | Forward primer | Reverse primer |
|---|---|---|---|---|---|---|---|
| 17 | rs4701997 | DNAH5 | 5 | 0.4878 | SNP Missense Variant | TGTGGTTAATCTCTGGGGAT (SEQ. ID. NO: 33) | AGCCCTACAGTTTGACCCTA (SEQ. ID. NO: 34) |
| 18 | rs251022 | PCDHGA10 | 5 | 0.4357 | SNP- 500B Downstream Variant (VNTR) | ACACACACACACGCAATTCGG (SEQ. ID. NO: 35) | ATGAGCTGAGGTGGGTGCTG (SEQ. ID. NO: 36) |
| 19 | rs714459 | SNX18 | 5 | 0.4922 | SNP | GGCAGCAATGTCATTACAGC (SEQ. ID. NO: 37) | GGCTCATTTCAGATCTGGCT (SEQ. ID. NO: 38) |
| 20 | rs1801020 | SLC34A1 | 5 | 0.4724 | SNP - 5'UTR Variant | CCACTTGGCTTTCCACAAAC (SEQ. ID. NO: 39) | CGATCTGTTGCTAGTCTGCA (SEQ. ID. NO: 40) |
| 21 | rs2842949 | TPMT | 6 | 0.4149 | SNP | TGCTTGTGTATGTGAAGGCA (SEQ. ID. NO: 41) | GCCTTTGCCTGTGTAGAGAA (SEQ. ID. NO: 42) |
| 22 | rs657941 | TAB2 | 6 | 0.4988 | SNP | CAAACTCCAGTGTTGGCATG (SEQ. ID. NO: 43) | CACCCCAAAGCACTCTGTTA (SEQ. ID. NO: 44) |
| 23 | rs805294 | C6orf25 | 6 | 0.4986 | SNP | GTTCCTCTTGCCACACTCTT (SEQ. ID. NO: 45) | AATGTCAGCTGGGAAGACAC (SEQ. ID. NO: 46) |
| 24 | rs2523860 | | 6 | 0.4872 | SNP | CAGCCTCTGGTTCCAGGCCT (SEQ. ID. NO: 47) | GGAGAATCCCAGAAGCAGGCTGA (SEQ. ID. NO: 48) |
| 25 | rs2766535 | FKBP5 | 6 | 0.4641 | SNP | AACTTAGCTGCTCTTGCTTCAGT (SEQ. ID. NO: 49) | GTACCTGCCTTAACTCAGTATGATCTT (SEQ. ID. NO: 50) |
| 26 | rs1554497 | SDK1 | 7 | 0.4998 | SNP | ATTGCCAATGTTGGAGGTGT (SEQ. ID. NO: 51) | CTTGGGCTGCTTACAGAAGG (SEQ. ID. NO: 52) |
| 27 | rs35024671 | UMAD1 | 7 | 0.4986 | INDEL (Insertion/deletion) | CTTCACTTGGCTTCCTCCTT (SEQ. ID. NO: 53) | TGTGCAGGTTTCAAGGGATT (SEQ. ID. NO: 54) |
| 28 | rs7794745 | CNTNAP2 | 7 | 0.4946 | SNP | CAGAAAGGCAGAAATCGGGA (SEQ. ID. NO: 55) | AGCAGCCTTTCAACACTGAT (SEQ. ID. NO: 56) |
| 29 | rs15775 | KLHL7 | 7 | 0.4203 | SNP | ATGCATCTCTCTAAGCCCCT (SEQ. ID. NO: 57) | GGCAAAGCATTGTCGTAACA (SEQ. ID. NO: 58) |
| 30 | rs2002792 | IL6 | 7 | 0.4894 | SNP | GGTCAGGAGTTCAAGACCCG (SEQ. ID. NO: 59) | CCTTCCCTGTGCATGGTGAT (SEQ. ID. NO: 60) |
| 31 | rs2575694 | CTHRC1 | 8 | 0.4782 | SNP | AATTTGTGTCTCCATCGCCA (SEQ. ID. NO: 61) | CAATCCCCTCTCCCAAGTTG (SEQ. ID. NO: 62) |
| 32 | rs756627 | RECQL4 | 8 | 0.4006 | SNP Missense Variant | TGCTTGTGGAGTTCAGTGAG (SEQ. ID. NO: 63) | CACATCAGGCTTCCTCTGAG (SEQ. ID. NO: 64) |
| 33 | rs1800392 | WRN | 8 | 0.4712 | SNP | TGTTAATCTGGTGCCTTGCA (SEQ. ID. NO: 65) | CCACTATGAGCAACGGAGAG (SEQ. ID. NO: 66) |
| 34 | rs11794980 | LCN2 | 9 | 0.4792 | SNP | CCATCTCTCCCTCCCAAGGA (SEQ. ID. NO: 67) | CCGAAGTCAGCTCCTTGGTT (SEQ. ID. NO: 68) |

TABLE 1-continued

Set of markers of the invention:

| Sl. No. | rs IDs | Gene | Chr | MAF | Type | Forward primer | Reverse primer |
|---|---|---|---|---|---|---|---|
| 35 | rs10738924 | DCAF12 | 9 | 0.474 | SNP | CAGCACTTTAGGAGGCCAAG (SEQ. ID. NO: 69) | GGTTCAAGCGATTCTTCTGC (SEQ. ID. NO: 72) |
| 36 | rs1197943 | LINGO2 | 9 | 0.4515 | SNP | CTTCCCTTGCCCCTCTTCCA (SEQ. ID. NO: 71) | TGCTCTGTGGATCCCTGGAG (SEQ. ID. NO: 74) |
| 37 | rs4405241 | PAX2 | 10 | 0.4996 | SNP | CTCCCCATGGATATGCACTG (SEQ. ID. NO: 73) | AATTGTCCTGACACTGAGGC (SEQ. ID. NO: 75) |
| 38 | rs2704522 | COL13A1 | 10 | 0.4944 | SNP | TGCCATCATATGCATGCAGA (SEQ. ID. NO: 75) | ATGAAATTCACCTGCCCACA (SEQ. ID. NO: 77) |
| 39 | rs1512705 | CUBN | 10 | 0.4972 | SNP | TGGATCTGCCACTCAAAGTG (SEQ. ID. NO: 77) | TTTTAGCTCTGCCATCTCGG (SEQ. ID. NO: 78) |
| 40 | rs10734083 | | 10 | 0.4916 | SNP | GGCATCTGAATTCAAGCTTTGGTC (SEQ. ID. NO: 79) | TTCTTCTAGTTGGTCTGGTAGGCT (SEQ. ID. NO: 80) |
| 41 | rs1073525 | M-ARCH8 | 10 | 0.4533 | SNP | ACTCAGAAAGGTGGGAGGAT (SEQ. ID. NO: 81) | CCCTCACTTCGGTCAGTTTT (SEQ. ID. NO: 82) |
| 42 | rs668393 | KCNJ1 | 11 | 0.4986 | SNP | AGGTCTGCCATGTGAATGAC (SEQ. ID. NO: 83) | GCCATCAGCTAAGGTCTCTG (SEQ. ID. NO: 84) |
| 43 | rs1522662 | | 11 | 0.4816 | SNP | ACCCTGACCCTCAGTTCCTT (SEQ. ID. NO: 85) | AAGAGCCCTTATAAGGTGTGAGAAA (SEQ. ID. NO: 86) |
| 44 | rs481235 | SLC3A2 | 11 | 0.4872 | SNP | CGCCTGTAATCCCAACACTT (SEQ. ID. NO: 87) | AGAGTGCAATGGCTCGATCT (SEQ. ID. NO: 88) |
| 45 | rs2277312 | SLC22A11 | 11 | 0.4531 | SNP | GAGGCCTATGACCATCTGGC (SEQ. ID. NO: 89) | GCAGAGCCAGGTCACATTCT (SEQ. ID. NO: 90) |
| 46 | rs2043055 | IL18 | 11 | 0.4806 | SNP | CCACCTGAAAGCCAATGAGA (SEQ. ID. NO: 91) | CCACCTGAAAGCCAATGAGA (SEQ. ID. NO: 92) |
| 47 | rs10841697 | SLCO1B3 | 12 | 0.4946 | SNP | GCTTTTCCAGGCACACAGTG (SEQ. ID. NO: 93) | TTGGGCTTATGAGTGGGCAG (SEQ. ID. NO: 94) |
| 48 | rs657197 | ATXN2 | 12 | 0.4687 | SNP | CACTCACCCTTGTGGACCTT (SEQ. ID. NO: 95) | GCTGATGCAAAATCAAAGCA (SEQ. ID. NO: 96) |
| 49 | rs9554250 | FLT3 | 13 | 0.498 | SNP | TGTGAGCCATCCAAAACCTT (SEQ. ID. NO: 97) | AGCAATGTGTACTGTGGCTT (SEQ. ID. NO: 98) |
| 50 | rs7328030 | LINC02337 | 13 | 0.4673 | SNP | CAGCCAATTTCTTCCCTGGA (SEQ. ID. NO: 99) | AGGACTGGAAAACGTGACAG (SEQ. ID. NO: 100) |
| 51 | rs1626923 | SPTB | 14 | 0.4451 | SNP | TTTTGCAGTGGGTAGGACAG (SEQ. ID. NO: 101) | ACTGGCTTGAGCTTTCCATT (SEQ. ID. NO: 102) |
| 52 | rs978511 | | 14 | 0.48 | SNP | GGCATGTTGATGGATGGGAT (SEQ. ID. NO: 103) | TTGCTGACAGTAGAACTCGC (SEQ. ID. NO: 104) |

TABLE 1-continued

Set of markers of the invention:

| Sl. No. | rs IDs | Gene | Chr | MAF | Type | Forward primer | Reverse primer |
|---|---|---|---|---|---|---|---|
| 53 | rs741761 | SEMA7A | 15 | 0.495 | SNP Missense Variant | TGCTGATCCTCTTTCGTCCT (SEQ. ID. NO: 105) | TCCCTCAGACCAGGACAATC (SEQ. ID. NO: 106) |
| 54 | rs10162971 | NR2F2-AS1 | 15 | 0.4964 | SNP | ACTATCAAGCCCACAGGAGA (SEQ. ID. NO: 107) | GCTTAGATGAGGCCTTCTGG (SEQ. ID. NO: 108) |
| 55 | rs12449089 | ITGAM | 16 | 0.4573 | SNP | GCCCAGCTTGAATTGACCTA (SEQ. ID. NO: 109) | CAGCTAAATGGGAGGCTGAG (SEQ. ID. NO: 110) |
| 56 | rs7193058 | UMOD | 16 | 0.4781 | SNP | CACTCACAGTGCCATCCATC (SEQ. ID. NO: 111) | CCATTCCTGGAGCTCACAAC (SEQ. ID. NO: 112) |
| 57 | rs11866418 | SOX8 | 16 | 0.4808 | SNP 3'UTR Variant | TCTACCAGTACCCCTGCTTC (SEQ. ID. NO: 113) | GAGGGAATGTGGCCTTGAG (SEQ. ID. NO: 114) |
| 58 | rs4323 | ACE | 17 | 0.4872 | SNP | AGGCCAACTGGAACTACAAC (SEQ. ID. NO: 115) | CTTCAAGTGATCCTCCCACC (SEQ. ID. NO: 116) |
| 59 | rs2159132 | COX10 | 17 | 0.4918 | SNP | CACAATGACAAGCTCAGGGA (SEQ. ID. NO: 117) | TTCTGGCCTTTACAGTTGGG (SEQ. ID. NO: 118) |
| 60 | rs150384 | NEDD4L | 18 | 0.4998 | SNP | GCGATGATGTCTCTGAGGCA (SEQ. ID. NO: 119) | ACAGACCCTGCCCACAAAAA (SEQ. ID. NO: 120) |
| 61 | rs3909244 | DLGAP1 | 18 | 0.4898 | SNP | TGGTTAAACTGTAGTACATCCATGGA (SEQ. ID. NO: 121) | ACCTTTTGGGACTGGCTTTCT (SEQ. ID. NO: 122) |
| 62 | rs12459052 | SLC7A9 | 19 | 0.4956 | SNP | TCCACATGTCAGGTGTCTGC (SEQ. ID. NO: 123) | GAGATGGGGTTTCACCGTGT (SEQ. ID. NO: 124) |
| 63 | rs67233828 | TGFB1 | 19 | 0.4878 | INDEL (Insertion/deletion), Intron variant | CTAGGCTCCTACAATGTGCC (SEQ. ID. NO: 125) | GCCGAGGTGGGTGGAT (SEQ. ID. NO: 126) |
| 64 | rs3918251 | MMP9 | 20 | 0.4938 | SNP | GAGTCGAAATCTCTGGGGCC (SEQ. ID. NO: 127) | GGACACCCCATATCGCAGAG (SEQ. ID. NO: 128) |
| 65 | rs2327088 | PLCB1 | 20 | 0.4517 | SNP | CCGATGCTGCTGAGGATAAA (SEQ. ID. NO: 129) | TCCAGTGTGCAAAGACTCTG (SEQ. ID. NO: 130) |
| 66 | rs1051266 | SLC19A1 | 21 | 0.4886 | SNP Missense Variant | TGGCCCCAAACCCTAAATTT (SEQ. ID. NO: 131) | CCGTAGAAGCAAAGGTAGCA (SEQ. ID. NO: 132) |
| 67 | rs2742630 | UPK3A | 22 | 0.4986 | SNP - 2KB upstream variant | CCTTGCCCCTCTTCTGTTGT (SEQ. ID. NO: 133) | CCCACTTGGAGCCTCAGTTT (SEQ. ID. NO: 134) |
| 68 | rs1801198 | TCN2 | 22 | 0.4203 | SNP Missense Variant | TGTTGCCCTTCTTCTCCAAG (SEQ. ID. NO: 135) | AGGTCTTGTGGTTCAGAACG (SEQ. ID. NO: 136) |
| 69 | rs6609533 | TIMP1 | X | 0.4734 | SNP Missense Variant | AATGGTCCCACTGGAAATGG (SEQ. ID. NO: 137) | TTAGGGAACAGCACTTTGGG (SEQ. ID. NO: 138) |
| 70 | rs2298065 | EFHC2 | X | 0.4185 | non-coding Transcript Variant | CATCCAAAGGTGGCACTTGC (SEQ. ID. NO: 139) | ACGTTGCAGCCATACAGACA (SEQ. ID. NO: 140) |

TABLE 1-continued

Set of markers of the invention:

| Sl. No. | rs IDs | Gene | C hr | MAF | Type | Forward primer | Reverse primer |
|---|---|---|---|---|---|---|---|
| 71 | | SRY | Y | | | TTGTGCAGC CATCACCTCT (SEQ. ID. NO: 141) | AAATCAGATT AATGGTTGCT (SEQ. ID. NO: 142) |

The transplant organ status of the transplant recipients was monitored until the rejection outcome and the frequency of monitoring the status is determined based on the transplant organ and the ratio of cut off values over time.

EXAMPLES

The invention is illustrated by various examples which are not meant to limit the scope of the invention in any manner. All the embodiments that may be obvious to a skilled person in view of the disclosure would fall within the scope of the present invention.

Example 1

STEP-1: Sample Collection and Separation of Plasma 5 ml of peripheral blood was collected by venipuncture into an EDTA-coated collection tube both from the donor and the recipient.

Urine samples were prepared by allowing it to stand until all the debris is settled and the clear upper layer is taken for analysis.

From this, 2 ml of blood was centrifuged at 5000 rpm for 10 min and plasma was carefully removed from the top and stored at −20° C. for further use.

STEP-2: Isolation of Circulating Cell-Free DNA, Genomic DNA:

2(a) Isolation of Circulating Cell-Free DNA (ccfDNA):

The circulating cell-free DNA (ccfDNA) is isolated from plasma following the manufacturer's instructions of EpiQuik Circulating cell-free DNA Isolation kit, Epigentek Group Inc. USA. The ccfDNA was isolated by adding 0.5 ml of plasma with 24 µl of ccfDNA capture Enhancer; 900 µl of Capture Buffer and 50 µl ccfDNA Capture Beads into 1.7 ml micro centrifuge tube. The solution was mixed well repeated pipetting at least 20 times and incubated at room temperature for 10 minutes. The solution was centrifuged at 12000 rpm for 5 minutes. The DNA release solution was prepared by mixing 2 µl of proteinase K with 40 µl of digestion solution. The supernatant was discarded and 40 µl of DNA release solution is added to the tube and beads are resuspended, incubated at 55° C. for 10 minutes. The tubes were placed on a magnetic stirrer and the supernatant containing the DNA was transferred to a tube containing MQ binding beads and 2× bead solution. It was mixed thoroughly by pipetting at least 10 times and incubated for 5 minutes at room temperature to allow the DNA to bind to the beads. Again, the tube is placed on a magnetic stand and the beads are resuspended in 200 µl of ethanol. The step was repeated twice, and ethanol was removed by airdrying. The DNA was eluted with 20 µl of elution buffer, and finally the cell free DNA was isolated.

2(b) Isolation of Whole Genomic DNA:

The Genomic DNA was isolated using Mag Attract Blood DNA Kit, Qiagen, USA, and the protocol followed was as per the manufacturer's instructions as given below: 500 µl of blood sample is taken in a sterile micro centrifuge tube and 1 ml of Blood Lysis Buffer— 1 was added. 50 µl of solution A was added and the contents were mixed by inverting the tube for 4-5 times and incubated at room temperature for 5 minutes. The samples were centrifuged at 8000 rpm for 5 minutes. Supernatant was discarded and the pellet was resuspend in the Blood Lysis Buffer— 1 by pipette mixing. The samples were centrifuged at 8000 rpm for 5 minutes and the previous steps were repeated. 20 µl of RNase A Solution was added to the resuspended pellet and incubated at room temperature for 15 minutes; followed by addition of 20 µl of Proteinase K. The sample was incubated at 56° C. for 10 minutes. To the lysate 350 µl of Blood Magna Mix— 3 was added and the contents are mixed by inverting the tube for 10-12 times. The lysate was incubated at room temperature for 5 minutes and placed on *magna* stand for 2 minutes or until solution appear clear. The supernatant was discarded without distributing the pellet. 500 µl of Blood Wash Buffer— 4 was added to the pellet and repeatedly washed with resuspended in blood wash buffer 5 to get the pellet which is then airdried. The pellet was resuspended in nuclease free water, incubated at 65° C. for 5 minutes. The tube is allowed to stand and the supernatant containing the DNA was isolated.

2(c) Quality Check Through Quantification of Isolated DNA:

The isolated DNA (Cell-Free DNA or Whole Genomic DNA) are quantified for the concentration and quality by Nano-Drop as per the protocol given below:

1 µl of isolated DNA (Cell-free DNA or Whole Genomic DNA) is placed on the Nano-Drop Spectrophotometer (Thermofisher Scientific) and the ratio of the readings at 260 nm and 280 nm is used for quantifying the isolated DNA.

Example 2

PCR Amplification and Determination of Total ccfDNA Value:

Total ccfDNA was quantified using multi locus LIPA2 regions. LIPA2 is a human Long Interspersed Element (LINE) of the class L1, that is well interspersed throughout the human genome. Reaction mixture for each LIPA-qPCR (90 bp and 222 bp amplicons) contained 3 µl DNA template, 0.5 µl of the each forward and reverse primer, 0.4 µl Rox as passive reference dye, 10 µl SYBR Green Master Mix (KAPA) and made up to total reaction volume of 20 µl with 95° C. for 1 min, followed by 40 cycles of 95° C. for 15 s. and annealing at 64° C. for 1 min in Stepone plus Real-Time PCR. System (Applied Biosystems, USA).

LIPA-qPCR reactions were standardized using 10 healthy control samples to yield the total ccfDNA results. The "control-value" is an average of total ccfDNA value of the ccfDNA levels of 10 healthy control and used as the standard. "Control Value" of the total ccfDNA of healthy subject is <7.7 ng/µl. The total ccfDNA of clinically stable and healthy post-transplant subjects was found to be less than 9.63 ng/µl and the total ccfDNA value above 9.63 ng/µl in a is considered to be significantly high.

In addition to this, melting curve was performed after each PCR reaction to ensure the amplification of a single peak for all samples. The integrity index is determined as the ratio of long fragments to that of short fragment of DNA. The Integrity Index of the DNA confirms the girth or the density of the DNA.

Example 3

PCR Amplification and Determination of the Donor-Derived ccfDNA.

The donor derived ccfDNA amplification is performed by DDPCR for the identification of the organ transplant status in the transplant recipient. Firstly, screening of all the High-MAF SNPs was done in both genomic DNA as well as the circulating cell-free DNA using Real-Time PCR. In this step, the SNPs that have heterozygous genotype in the recipient are filtered out and eliminated, since they cannot be used for quantification in DDPCR. In the next step, the pre-amplified ccfDNA is used as the template, and the candidate SNPs are filtered out and the assay is set for the individual patient. The SNPs which are homozygous in the recipient and that could be either heterozygous or homozygous on the allele in the graft and is preferably heterologous between the recipient and the graft is chosen as the final candidate SNPs. This step is performed as a DDPCR assay.

All homozygous SNPs were subsequently used to genotype the recipient's ccfDNA enabling the measurement of the donor derived ccfDNA fraction by using a hydrolysis based SNP assay in combination with DDPCR. The number of candidate SNPs obtained ranged between 2 and 9 with a minimum of 3 SNPs per patient in the above method. The average of the 3 SNPs determined is measured as absolute copy numbers (copies/µl) and is expressed as percentage of donor-derived ccfDNA markers to the recipient derived markers. The percentages and numbers of assays given for each selection step are calculated for a minor allele frequency of 0.5 and can vary between individual patients. The percentage of donor-derived ccfDNA differs significantly between various organ transplants as given below.

| Type of transplant (Tx) | Mean Cut-off Value of Donor-Derived ccfDNA in the transplant recipients | Variability (in terms of values) | Outcome |
| --- | --- | --- | --- |
| Heart Tx | 0.1% to 3.0% | +/−0.9% | Healthy Tx Patients |
| Heart Tx | 2.75% to 4.55% | +/−1.8% | Acute Rejection in Heart Tx |
| Liver Tx | Less than 15% | +/−5% | Healthy Liver transplant |
| Liver Tx | 30%-60% | +/−10% | Liver Transplant Rejection |
| Kidney Tx | 0.3 to 3.5% | +/−1.1% | Healthy Kidney Tx |
| Kidney Tx | Over 3% to 5.5% | +/−1.5% | Acute Rejection |

Example 4

SNP Selection:

For arriving at the candidate 71 SNPs with high Minor Allele Frequency (minor allele frequency [MAF>40] or MAF>0.4000 an extensive bioinformatics analysis was performed. It includes the selection of the genes that are proven to play role in tissue rejection and necrosis as well as the SNP markers that are proven to help differentiate between two individuals. The SNPS having high MAF in both rejection-related genes as well as in the markers that are proven to differentiate between two unrelated individuals, and that is spanning across all the chromosomes is selected.

Example 5

Sample Validation

A total of 19 patients (13 heart transplant, 5 kidney transplant and 1 kidney+pancreas transplant) was used for validation. From the group of 13 patients who had undergone heart transplant, 11 patients had successful 1 year survival and 2 patients died within 10 days of heart transplant. In 5 kidney and 1 patient who had undergone combined kidney and pancreas transplant had a healthy 1 year survival rate. The below is the table of only the total ccfDNA in determining transplant outcome and the infection status.

| S no | Type of Transplant | No of patients | Actual value | Cutoff value | Outcome prediction |
| --- | --- | --- | --- | --- | --- |
| 1. | Heart Tx | 11 | 2-9 ng/ul | 9.63 ng/ul | Clinically stable and healthy |
| 2. | Heart Tx | 1 | 15.8 ng/ul | 9.63 ng/ul | Immediate Rejection, patient expired. |
| 3. | Heart Tx | 1 | 8.5 ng/ul | 9.63 ng/ul | No rejection found, but patient expired of cardiac arrest. |
| 5. | Kidney Tx | 3 | 6-8 ng/ul | 9.63 ng/ul | Clinically stable and Healthy |
| 6. | Kidney Tx | 1 | 12.24 ng/ul | 9.63 ng/ul | High total cfDNA level, Suspected Rejection, elevated creatinine levels, anti-rejection prophylaxis. |
| 7. | Kidney + Pancreas Tx | 1 | 6.8 ng/ul | 9.63 ng/ul | No Rejection Found. Clinically stable, healthy. |

Advantages of the Invention

The method is cost-effective, rapid and absolute quantification of nucleic acids by counting molecules and also have superior analytical precision compared to conventional PCR or qPCR based detection methods or next generation (NGS) sequencing. The method described herein with the analysis of amplified marker sequences of the donor derived circulating cell free nucleic acid with DDPCR has a specificity between 90% and 100%.

The SNP selected have high MAF, and it includes SNPs taken from genes that have been proven to play role in rejection, ie, the SNPs with high MAF includes SNPs from the genes that are clinically proven to be found playing role in rejection. The selected 71 SNPs covers the entire genome, including X and Y chromosomes. This way of selection minimizes the error rate.

There is no requirement of Donor DNA to detect the donor-derived ccf-DNA and it is done with the transplant recipients.

For both gDNA and ccf-DNA are together screened for eliminating the heterozygous genotype in the transplant recipients. This saves a lot in reagents and time, there by making the assay cost-effective.

The value of rotal ccfDNA itself is used as marker to evaluate the transplant status and is clinically validated, as elevated total ccfDNA can be a hallmark of rejection or an infection.

REFERENCES

1. Breitbach S, Tug S, Helmig S, Zahn D, Kubiak T, Michal M, Gori T, Ehlert T, Beiter T, Simon P, "Direct Quantification of Cell-Free, Circulating DNA from Unpurified Plasma", PLoS ONE 9(3):2014, e87838.
2. A. J. Pakstis, W. C. Speed, J. R. Kidd, K. K. Kidd, "SNPs for Individual Identification", Science Direct, Genetic Supplement, 2008, pp 479-481.
3. Thomas M. Snydera, b, Kiran K. Khushc, Hannah A. Valantinec, 1, and Stephen R. Quake, "Universal noninvasive detection of Solid-organ transplant rejection", PNAS Vol 108, 2011, pp 6229-6234.
4. E. M. Gielis, K. J. Ledeganck, B. Y. De Winter, J. Del Favero, J.-L. Bosmans, F. H. J. Claas, D. Abramowicz, M. Eikmans, "Cell-Free DNA: An Upcoming Biomarker in Transplantation", American Journal of Transplantation 2015; 15: pp2541-2551
5. Beck J, Oellerich M, Schulz U, Schauerte V, Reinhard L, Fuchs U, Knabbe C, Zittermann A, Olbricht C, Gummert J F, Shipkova M. "Donor-derived cell-free DNA is a novel universal biomarker for allograft rejection in solid organ transplantation" In Transplantation proceedings 2015 Oct. 1, (Vol. 47, No. 8, pp. 2400-2403). Elsevier.
6. Huggett J F, Whale A. "Digital PCR as a novel technology and its potential implications for molecular diagnostics", Clinical Chemistry 59:12, 2013, pp 1691-1693.
7. Beck J, Bierau S, Balzer S, Andag R, Kanzow P, Schmitz J, Gaedcke J, Moerer O, Slotta J E. Walson P, Kollmar O. "Digital Droplet PCR for rapid quantification of donor DNA in the Circulation of transplant recipients as a potential universal biomarker of Graft Injury" Clinical chemistry. 59:12, 2013, pp 1732-1741
8. Silke Roedder, Matthew Vitalone, Purvesh Khatri and Minnie M Sarwal, "Biomarkers in solid organ transplantation: establishing personalized transplantation medicine", Genome Medicine, 3:37, 2011
9. De Vlaminck I, Martin L, Kertesz M, Patel K, Kowarsky M, Strehl C, Cohen G, Luikart H. Neff N F, Okamoto J, Nicolls M R. "Noninvasive monitoring of infection and rejection after lung transplantation", Proceedings of the National Academy of Sciences. 2015 Oct. 27; 112(43): 13336-41.
10. Macher H C, Suárez-Artacho G, Guerrero J M, Gómez-Bravo M A, Álvarez-Gómez S, Bernal-Bellido C, Dominguez-Pascual I, Rubio A. Monitoring of transplanted liver health by quantification of organ-specific genomic marker in circulating DNA from receptor. PLoSOne. 2014; 9(12):e113987.
11. Sigdel T K, Vitalone M J, Tran T Q, Dai H, Hsieh S C, Salvatierra O, Sarwal M M. "A rapid noninvasive assay for the detection of renal transplant injury", Transplantation. 2013 July; 96(1):97.
12. Vijayakrishna K. Gadi, J. Lee Nelson, Nicholas D. Boespflug, Katherine A. Guthrie, Christian A. Kuhr, "Soluble Donor DNA Concentrations in Recipient Serum Correlate with Pancreas-Kidney Rejection Clinical Chemistry" 52:3, 2006, pp379-382
13. Oellerich M, Beck J, Kanzow P, Schmitz J, Kollmar O, Walson P D, Schütz E. Graft-derived cell-free DNA as a marker of graft integrity after transplantation. In Personalized Immunosuppression in Transplantation 2016 (pp. 153-176),
14. Grskovic M, Hiller D J, Eubank L A, Sninsky J J, Christopherson C, Collins J P, Thompson K, Song M, Wang Y S, Ross D. Nelles M J, "Validation of a clinical-grade assay to measure donor-derived cell-free DNA in solid organ transplant recipients" The Journal of Molecular Diagnostics. 2016 Nov. 1; 18(6):890-902,
15. Adamek M, Opelz G, Klein K, Morath C, Tran T H. "A fast and simple method for detecting and quantifying donor-derived cell-free DNA in sera of solid organ transplant recipients as a biomarker for graft function", Clinical Chemistry and Laboratory Medicine (CCLM). 2016 Jul. 1; 54(7):1147-55
16. De Vlaminck I, Hannah A. Valantine, Thomas M. Snyder, Calvin Strehl, Garrett Cohen, Helen Luikart, Norma F. Neff, Jennifer Okamoto, Daniel Bernstein, Dana Weisshaar, Stephen R. Quake, Kiran K. Khush, "Circulating cell-free DNA enables noninvasive diagnosis of heart transplant rejection", Science translational medicine, June 2014, 6(241):241ra77
17. Steven Hoffmann, et. al., "Donor genomics influence graft events: The effect of donor polymorphisms on acute rejection and chronic allograft nephropathy", Kidney International, Vol. 66, 2004, pp. 1686-1693.
18. Oellerich M, Walson P D, Beck J, Schmitz J, Kollmar O, Schütz E. Graft-derived cell-free DNA as a marker of transplant graft injury. Therapeutic drug monitoring. 2016 Apr. 1; 38:S75-9.
19. Lee H, Park Y M, We Y M, Han D J, Seo J W, Moon H, Lee Y H, Kim Y G, Moon J Y, Lee S H, Lee J K. Evaluation of digital PCR as a technique for monitoring acute rejection in kidney transplantation. Genomics & informatics. 2017 March; 15(1):2.
20. Schütz E, Fischer A, Beck J, Harden M, Koch M, Wuensch T, Stockmann M. Nashan B, Kollmar O, Matthaei J, Kanzow P. Graft-derived cell-free DNA, a noninvasive early rejection and graft damage marker in liver transplantation: A prospective, observational, multicenter cohort study. PLoS medicine. 2017, 14(4):e1002286.
21. Grskovic M, Christie B, Hiller D, Woodward R, Yee J, Vincenti F. Donor-derived cell-free DNA in plasma increases with rejection and decreases after treatment in kidney transplant recipients. J Am Soc Nephrol. 2015; 26:1141

22. Crespo-Leiro M G, Barge-Caballero G, Couto-Mallon D. Noninvasive monitoring of acute and chronic rejection in heart transplantation. Current opinion in cardiology, 2017 May 1; 32(4308-15.
23. Deng M C. The AlloMap™ genomic biomarker story: 10 years after. Clinical transplantation. 2017 March; 31(3): e12900.
24. Kobashigawa J, Grskovic M, Dedrick R, Gundel K, Woodward R, Vanhaecke J, Crespo-Leiro M G, Stypmann J, Deng M C, Starling R. Increased plasma levels of cell-free DNA correlate with rejection in heart transplant recipients. The Journal of Heart and Lung Transplantation. 2014 Apr. 1; 33(4):S14.

The invention claimed is:

1. A method of assessing the status of a transplanted organ in the transplant recipients, comprising of:
   collecting a biological sample from a recipient, a subject who has received an organ transplant from a donor, and identifying one or more markers of the genomic DNA of the recipient having homozygous genotype, referred as recipient-derived marker sequences, by screening all listed markers using each of the recited primer pairs;
   (ii) identifying said one or more marker sequences from the transplant donor in the recipient and having heterozygous genotype, referred as donor-derived marker sequences by analyzing the circulating cell free nucleic acids of the transplant recipient using each of the primer pairs by digital droplet polymerase chain reaction (DDPCR);
   (iii) calculating a ratio of the donor derived marker sequences to the recipient-derived marker sequences expressed in terms of percent; and
   (iv) assessing the organ status of the transplant recipients on comparison of the calculated percent obtained in step (iii) with the cut off value,
   wherein the markers are rs2493132, rs6667487, rs553921764, rs4233335, rs10900556, rs1449265, rs7603052, rs1317808, rs2229813, rs4851521, rs7653603, rs6791557, rs7652776, rs9131, rs352007, rs1818782, rs4701997, rs251022, rs714459, rs1801020, rs2842949, rs657941, rs805294, rs2523860, rs2766535, rs1554497, rs35024671, rs7794745, rs15775, rs2002792, rs2575694, rs756627, rs1800392, rs11794980, rs10738924, rs1197943, rs4405241, rs2704522, rs1512705, rs10734083, rs1073525, rs668393, rs1522662, rs481235, rs2277312, rs2043055, rs10841697, rs657197, rs9554250, rs7328030, rs1626923, rs978511, rs741761, rs10162971, rs12449089, rs7193058, rs11866418, rs4323, rs2159132, rs150384, rs3909244, rs12459052, rs67233828, rs3918251, rs2327088, rs1051266, rs2742630, rs1801198, rs6609533, rs2298065, and S1.No. 71, wherein each of the markers is identified by a pair of primers comprising nucleic acid sequences as follows: rs2493132 is identified by a pair of primers comprising nucleic acid sequences SEQ ID NO: 1 and 2, rs6667487 by primers having SEQ ID NO: 3 and 4, rs553921764 by primers having SEQ ID NO: 5 and 6, rs4233335 by primers having SEQ ID NO: 7 and 8, rs10900556 by primers having SEQ ID NO: 9 and 10, rs1449265 by primers having SEQ ID NO: 11 and 12, rs7603052 by primers having SEQ ID NO: 13 and 14, rs1317808 by primers having SEQ ID NO: 15 and 16, rs2229813 by primers having SEQ ID NO: 17 and 18, rs4851521 by primers having SEQ ID NO: 19 and 20, rs7653603 by primers having SEQ ID NO: 21 and 22, rs6791557 by primers having SEQ ID NO: 23 and 24, rs7652776 by primers having SEQ ID NO: 25 and 26, rs9131 by primers having SEQ ID NO: 27 and 28, rs352007 by primers having SEQ ID NO: 29 and 30, rs1818782 by primers having SEQ ID NO: 31 and 32, rs4701997 by primers having SEQ ID NO: 33 and 34, rs251022 by primers having SEQ ID NO: 35 and 36, rs714459 by primers having SEQ ID NO: 37 and 38, rs1801020 by primers having SEQ ID NO: 39 and 40, rs2842949 by primers having SEQ ID NO: 41 and 42, rs657941 by primers having SEQ ID NO: 43 and 44, rs805294 by primers having SEQ ID NO: 45 and 46, rs2523860 by primers having SEQ ID NO: 47 and 48, rs2766535 by primers having SEQ ID NO: 49 and 50, rs1554497 by primers having SEQ ID NO: 51 and 52, rs35024671 by primers having SEQ ID NO: 53 and 54, rs7794745 by primers having SEQ ID NO: 55 and 56, rs15775 by primers having SEQ ID NO: 57 and 58, rs2002792 by primers having SEQ ID NO: 59 and 60, rs2575694 by primers having SEQ ID NO: 61 and 62, rs756627 by primers having SEQ ID NO: 63 and 64, rs1800392 by primers having SEQ ID NO: 65 and 66, rs11794980 by primers having SEQ ID NO: 67 and 68, rs10738924 by primers having SEQ ID NO: 69 and 70, rs1197943 by primers having SEQ ID NO: 71 and 72, rs4405241 by primers having SEQ ID NO: 73 and 74, rs2704522 by primers having SEQ ID NO: 75 and 76, rs1512705 by primers having SEQ ID NO: 77 and 78, rs10734083 by primers having SEQ ID NO: 79 and 80, rs1073525 by primers having SEQ ID NO: 81 and 82, rs668393 by primers having SEQ ID NO: 83 and 84, rs1522662 by primers having SEQ ID NO: 85 and 86, rs481235 by primers having SEQ ID NO: 87 and 88, rs2277312 by primers having SEQ ID NO: 89 and 90, rs2043055 by primers having SEQ ID NO: 91 and 92, rs10841697 by primers having SEQ ID NO: 93 and 94, rs657197 by primers having SEQ ID NO: 95 and 96, rs9554250 by primers having SEQ ID NO: 97 and 98, rs7328030 by primers having SEQ ID NO: 99 and 100, rs1626923 by primers having SEQ ID NO: 101 and 102, rs978511 by primers having SEQ ID NO: 103 and 104, rs741761 by primers having SEQ ID NO: 105 and 106, rs10162971 by primers having SEQ ID NO: 107 and 108, rs12449089 by primers having SEQ ID NO: 109 and 110, rs7193058 by primers having SEQ ID NO: 111 and 112, rs11866418 by primers having SEQ ID NO: 113 and 114, rs4323 by primers having SEQ ID NO: 115 and 116, rs2159132 by primers having SEQ ID NO: 117 and 118, rs150384 by primers having SEQ ID NO: 119 and 120, rs3909244 by primers having SEQ ID NO: 121 and 122, rs12459052 by primers having SEQ ID NO: 123 and 124, rs67233828 by primers having SEQ ID NO: 125 and 126, rs3918251 by primers having SEQ ID NO: 127 and 128, rs2327088 by primers having SEQ ID NO: 129 and 130, rs1051266 by primers having SEQ ID NO: 131 and 132, rs2742630 by primers having SEQ ID NO: 133 and 134, rs1801198 by primers having SEQ ID NO: 135 and 136, rs6609533 by primers having SEQ ID NO: 137 and 138, rs2298065 by primers having SEQ ID NO: 139 and 140, and S1.No. 71 by primers having SEQ ID NO: 141 and 142.

2. The method according to claim 1, wherein the identified markers are ranged between 3 and 9 with a minimum of 3 markers per recipient and wherein average of the markers, measured as absolute copy numbers (copies/µl), is determined and expressed as percentage of donor-derived ccfDNA markers to the recipient derived markers.

3. The method according to claim 1, wherein the cut off value for monitoring the status of the transplanted organ of the transplant recipient varies with the transplant type and is the range of 0.1% to 15%.

4. The method according to claim 1, wherein the biological sample is selected from whole blood, plasma, serum or urine.

5. The method according to claim 1, wherein the transplant is selected from an organ transplant or a skin/tissue transplant.

6. The method according to claim 1, wherein the organ transplant is selected from one of kidney transplant, heart transplant, liver transplant, pancreas transplant, lungs transplant, intestine transplant, bone marrow or thymus transplant or a combination of more than one organ transplant.

7. A method of monitoring the status of a transplanted organ in transplant recipients comprising assessing the transplant organ status of the transplant recipients by the method according to claim 1 for a plurality of times, thereby monitoring the transplant organ status.

8. The method according to claim 7, wherein the monitoring of the transplant organ status of the transplant recipients is performed until the rejection of the organ occurs.

9. The method according to claim 7, wherein the frequency of assessing the transplant organ status of the transplant recipients is a function of time determined based on the transplanted organ and the ratio of the donor derived marker sequences to the recipient-derived marker sequences expressed in terms of percent over time.

* * * * *

SEQUENCE LISTING

```
<160> NUMBER OF SEQ ID NOS: 142

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 1
aaagacgctg ggatttgaca                                              20

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: Artificially synthesized Reverse primer

<400> SEQUENCE: 2
gtctcccttc gaaagagagc                                              20

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 3
tcattgaagt caggctgtgc                                              20

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: Artificially synthesized Reverse primer

<400> SEQUENCE: 4
ggtgagcaac ttggaagctc                                              20

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: Artificially synthesized Forward primer

<400> SEQUENCE: 5
tcctcaccct actgtacacc                                              20

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: Artificially synthesized Reverse primer
```

```
<400> SEQUENCE: 6
acacagggag gatgagtgat                                                    20

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 7
attctggtct ccgctgtttc                                                    20

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 8
attctggtct ccgctgtttc                                                    20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: Artificially synthesized Forward primer

<400> SEQUENCE: 9
gtctggaatc atgggcaagt                                                    20

<210> SEQ ID NO 10
<211> LENGTH: 20
<212> TYPE: DNA
<213> ORGANISM: ARTIFICIAL SEQUENCE
<220> FEATURE:
<223> OTHER INFORMATION: Artificially synthesized Reverse primer

<400> SEQUENCE: 10
acctagggga tgctaaggtt                                                    20

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 11
ctgagaggca ctcatgtgga                                                    20

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: Artificially synthesized Reverse primer

<400> SEQUENCE: 12
aagaaggagg caatgcagaa                                                    20

<210> SEQ ID NO 13
<211> LENGTH: 20
```

-continued

```
<212> TYPE: DNA
<213> ORGANISM: ARTIFICIAL SEQUENCE
<220> FEATURE:
<223> OTHER INFORMATION: Artificially synthesized forward primer

<400> SEQUENCE: 13
gaaaagggtt gagcctgtca                                            20

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: Artificially synthesized Reverse primer

<400> SEQUENCE: 14
tcatcacggg tactgtgagc                                            20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 15
gccaccttag cctcccaaag                                            20

<210> SEQ ID NO 16
<211> LENGTH: 30
<212> TYPE: DNA
<213> ORGANISM: ARTIFICIAL SEQUENCE
<220> FEATURE:
<223> OTHER INFORMATION: Artificially synthesized Reverse primer

<400> SEQUENCE: 16
agggtgactg tattaattat tgttcaaact                                 30

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 17
tccagtcctt tgtctccaga                                            20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 18
agtgcggcct gaaagaaata                                            20

<210> SEQ ID NO 19
<211> LENGTH: 20
<212> TYPE: DNA
<213> ORGANISM: ARTIFICIAL SEQUENCE
<220> FEATURE:
<223> OTHER INFORMATION: Artificially synthesized

<400> SEQUENCE: 19
```
cacccacaac tctgctgtaa                                              20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: Artificiallly synthesized reverse primer

<400> SEQUENCE: 20
gatgttctgg atccctcagc                                              20

<210> SEQ ID NO 21
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 21 agggggaaaaa gtcaaaggca                                             20

<210> SEQ ID NO 22
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 22
cctttcccga gtatgcactt                                              20

<210> SEQ ID NO 23
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 23
gaagatatgg gttgggtgca                                              20

<210> SEQ ID NO 24
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 24
gtcttccaac acccatgcta                                              20

<210> SEQ ID NO 25
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 25
gagggctttg gagtggaaat                                              20

<210> SEQ ID NO 26
<211> LENGTH: 20
<212> TYPE: DNA
<213> ORGANISM: ARTIFICIAL SEQUENCE

```
<220> FEATURE:
<223> OTHER INFORMATION: Artificially synthesized reverse primer

<400> SEQUENCE: 26
tccaaggttt gctcaagagg                                               20

<210> SEQ ID NO 27
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 27
ctgttgtgca gtcagctttc                                               20

<210> SEQ ID NO 28
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 28
catacatttc cctgccgtca                                               20

<210> SEQ ID NO 29
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 29
agcaaatgca cacacgtagg                                               20

<210> SEQ ID NO 30
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 30
atttgcaaac ccaaggactg                                               20

<210> SEQ ID NO 31
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 31
ccaagcacag ggtctcattt                                               20

<210> SEQ ID NO 32
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 32
gaaacccttc ttccctctgg                                               20
```

<210> SEQ ID NO 33
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 33
tgtggttaat ctctggggat                                          20

<210> SEQ ID NO 34
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 34
agccctacag tttgaccta                                           20

<210> SEQ ID NO 35
<211> LENGTH: 21
<212> TYPE: DNA
<213> ORGANISM: ARTIFICIAL SEQUENCE
<220> FEATURE:
<223> OTHER INFORMATION: Artificially synthesized forward primer

<400> SEQUENCE: 35
acacacacac acgcaattcg g                                        21

<210> SEQ ID NO 36
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 36
atgagctgag gtgggtgctg                                          20

<210> SEQ ID NO 37
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 37
ggcagcaatg tcattacagc                                          20

<210> SEQ ID NO 38
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 38
ggctcatttc agatctggct                                          20

<210> SEQ ID NO 39
<211> LENGTH: 20
<212> TYPE: DNA
<213> ORGANISM: ARTIFICIAL SEQUENCE
<220> FEATURE:
<223> OTHER INFORMATION: Artificially synthesized forward primer

```
<400> SEQUENCE: 39
ccacttggct ttccacaaac                                               20

<210> SEQ ID NO 40
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 40
cgatctgttg ctagtctgca                                               20

<210> SEQ ID NO 41
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 41
tgcttgtgta tgtgaaggca                                               20

<210> SEQ ID NO 42
<211> LENGTH: 20
<212> TYPE: DNA
<213> ORGANISM: ARTIFICIAL SEQUENCE
<220> FEATURE:
<223> OTHER INFORMATION: Artificially synthesised reverse primer

<400> SEQUENCE: 42
gcctttgcct gtgtagagaa                                               20

<210> SEQ ID NO 43
<211> LENGTH: 20
<212> TYPE: DNA
<213> ORGANISM: ARTIFICIAL SEQUENCE
<220> FEATURE:
<223> OTHER INFORMATION: Artificially sythesized forward primer

<400> SEQUENCE: 43
caaactccag tgttggcatg                                               20

<210> SEQ ID NO 44
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 44
caccccaaag cactctgtta                                               20

<210> SEQ ID NO 45
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 45
gttcctcttg ccacactctt                                               20

<210> SEQ ID NO 46
```

```
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 46
aatgtcagct gggaagacac                                              20

<210> SEQ ID NO 47
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 47
cagcctctgg ttccaggcct                                              20

<210> SEQ ID NO 48
<211> LENGTH: 23
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 48
ggagaatccc agaagcaggc tga                                          23

<210> SEQ ID NO 49
<211> LENGTH: 23
<212> TYPE: DNA
<213> ORGANISM: ARTIFICIAL SEQUENCE
<220> FEATURE:
<223> OTHER INFORMATION: Artificially synthesized forward primer

<400> SEQUENCE: 49
aacttagctg ctcttgcttc agt                                          23

<210> SEQ ID NO 50
<211> LENGTH: 27
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 50
gtacctgcct taactcagta tgatctt                                      27

<210> SEQ ID NO 51
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 51
attgccaatg ttggaggtgt                                              20

<210> SEQ ID NO 52
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 52
```
cttgggctgc ttacagaagg                                              20

<210> SEQ ID NO 53
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 53
cttcacttgg cttcctcctt                                              20

<210> SEQ ID NO 54
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 54
tgtgcaggtt tcaagggatt                                              20

<210> SEQ ID NO 55
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 55
cagaaaggca gaaatcggga                                              20

<210> SEQ ID NO 56
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 56
agcagccttt caacactgat                                              20

<210> SEQ ID NO 57
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 57
atgcatctct ctaagcccct                                              20

<210> SEQ ID NO 58
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 58
ggcaaagcat tgtcgtaaca                                              20

<210> SEQ ID NO 59
<211> LENGTH: 20
<212> TYPE: DNA

```
<213> ORGANISM: ARTIFICIAL SEQUENCE
<220> FEATURE:
<223> OTHER INFORMATION: Artificially synthesized forward primer

<400> SEQUENCE: 59
ggtcaggagt tcaagacccg                                               20

<210> SEQ ID NO 60
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 60
ccttccctgt gcatggtgat                                               20

<210> SEQ ID NO 61
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 61
aatttgtgtc tccatcgcca                                               20

<210> SEQ ID NO 62
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 62
caatcccctc tcccaagttg                                               20

<210> SEQ ID NO 63
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 63
tgcttgtgga gttcagtgag                                               20

<210> SEQ ID NO 64
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 64
cacatcaggc ttcctctgag                                               20

<210> SEQ ID NO 65
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 65
tgttaatctg gtgccttgca                                               20
```

-continued

<210> SEQ ID NO 66
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 66
ccactatgag caacggagag                                               20

<210> SEQ ID NO 67
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 67
ccatctctcc ctcccaagga                                               20

<210> SEQ ID NO 68
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 68
ccgaagtcag ctccttggtt                                               20

<210> SEQ ID NO 69
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 69
cagcacttta ggaggccaag                                               20

<210> SEQ ID NO 70
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 70
ggttcaagcg attcttctgc                                               20

<210> SEQ ID NO 71
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 71
cttcccttgc ccctcttcca                                               20

<210> SEQ ID NO 72
<211> LENGTH: 20
<212> TYPE: DNA
<213> ORGANISM: ARTIFICIAL SEQUENCE
<220> FEATURE:

<223> OTHER INFORMATION: Artificially synthesised reverse primer

<400> SEQUENCE: 72
tgctctgtgg atccctggag                                                20

<210> SEQ ID NO 73
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 73
ctccccatgg atatgcactg                                                20

<210> SEQ ID NO 74
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 74
aattgtcctg acactgaggc                                                20

<210> SEQ ID NO 75
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 75
tgccatcata tgcatgcaga                                                20

<210> SEQ ID NO 76
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 76
atgaaattca cctgcccaca                                                20

<210> SEQ ID NO 77
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 77
tggatctgcc actcaaagtg                                                20

<210> SEQ ID NO 78
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 78
ttttagctct gccatctcgg                                                20

```
<210> SEQ ID NO 79
<211> LENGTH: 24
<212> TYPE: DNA
<213> ORGANISM: ARTIFICIAL SEQUENCE
<220> FEATURE:
<223> OTHER INFORMATION: Artificially synthesized forward primer

<400> SEQUENCE: 79
ggcatctgaa ttcaagctttt ggtc                                         24

<210> SEQ ID NO 80
<211> LENGTH: 24
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 80
ttcttctagt tggtctggta ggct                                          24

<210> SEQ ID NO 81
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 81
actcagaaag gtgggaggat                                               20

<210> SEQ ID NO 82
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 82
ccctcacttc ggtcagtttt                                               20

<210> SEQ ID NO 83
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 83
aggtctgcca tgtgaatgac                                               20

<210> SEQ ID NO 84
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 84
gccatcagct aaggtctctg                                               20

<210> SEQ ID NO 85
<211> LENGTH: 20
<212> TYPE: DNA
<213> ORGANISM: ARTIFICIAL SEQUENCE
<220> FEATURE:
<223> OTHER INFORMATION: Artificially synthesized forward primer
```

```
<400> SEQUENCE: 85
accctgaccc tcagttcctt                                             20

<210> SEQ ID NO 86
<211> LENGTH: 25
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 86
aagagccctt ataaggtgtg agaaa                                       25

<210> SEQ ID NO 87
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 87
cgcctgtaat cccaacactt                                             20

<210> SEQ ID NO 88
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 88
agagtgcaat ggctcgatct                                             20

<210> SEQ ID NO 89
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 89
gaggcctatg accatctggc                                             20

<210> SEQ ID NO 90
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 90
gcagagccag gtcacattct                                             20

<210> SEQ ID NO 91
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 91
ccacctgaaa gccaatgaga                                             20

<210> SEQ ID NO 92
<211> LENGTH: 20
```

```
<212> TYPE: DNA
<213> ORGANISM: ARTIFICIAL SEQUENCE
<220> FEATURE:
<223> OTHER INFORMATION: Artiffically synthesized reverse primer

<400> SEQUENCE: 92
ccacctgaaa gccaatgaga                                              20

<210> SEQ ID NO 93
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 93
gcttttccag gcacacagtg                                              20

<210> SEQ ID NO 94
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 94
ttgggcttat gagtgggcag                                              20

<210> SEQ ID NO 95
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 95
cactcaccct tgtggacctt                                              20

<210> SEQ ID NO 96
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 96
gctgatgcaa aatcaaagca                                              20

<210> SEQ ID NO 97
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 97
tgtgagccat ccaaaacctt                                              20

<210> SEQ ID NO 98
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 98
```

```
agcaatgtgt actgtggctt                                          20

<210> SEQ ID NO 99
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 99
cagccaattt cttccctgga                                          20

<210> SEQ ID NO 100
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 100
aggactggaa aacgtgacag                                          20

<210> SEQ ID NO 101
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 101
ttttgcagtg ggtaggacag                                          20

<210> SEQ ID NO 102
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 102
actggcttga gctttccatt                                          20

<210> SEQ ID NO 103
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 103
ggcatgttga tggatgggat                                          20

<210> SEQ ID NO 104
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 104
ttgctgacag tagaactcgc                                          20

<210> SEQ ID NO 105
<211> LENGTH: 20
<212> TYPE: DNA
<213> ORGANISM: ARTIFICIAL SEQUENCE
```

```
<220> FEATURE:
<223> OTHER INFORMATION: Artificially synthesized forward primer

<400> SEQUENCE: 105
tgctgatcct ctttcgtcct                                              20

<210> SEQ ID NO 106
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 106
tccctcagac caggacaatc                                              20

<210> SEQ ID NO 107
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 107
actatcaagc ccacaggaga                                              20

<210> SEQ ID NO 108
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 108
gcttagatga ggccttctgg                                              20

<210> SEQ ID NO 109
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 109
gcccagcttg aattgaccta                                              20

<210> SEQ ID NO 110
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 110
cagctaaatg ggaggctgag                                              20

<210> SEQ ID NO 111
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 111
cactcacagt gccatccatc                                              20
```

<210> SEQ ID NO 112
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 112
ccattcctgg agctcacaac                                               20

<210> SEQ ID NO 113
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 113
tctaccagta cccctgcttc                                               20

<210> SEQ ID NO 114
<211> LENGTH: 19
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 114
gagggaatgt ggccttgag                                                19

<210> SEQ ID NO 115
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 115
aggccaactg gaactacaac                                               20

<210> SEQ ID NO 116
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 116
cttcaagtga tcctcccacc                                               20

<210> SEQ ID NO 117
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 117
cacaatgaca agctcaggga                                               20

<210> SEQ ID NO 118
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 118
ttctggcctt tacagttggg                                          20

<210> SEQ ID NO 119
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 119
gcgatgatgt ctctgaggca                                          20

<210> SEQ ID NO 120
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 120
acagaccctg cccacaaaaa                                          20

<210> SEQ ID NO 121
<211> LENGTH: 26
<212> TYPE: DNA
<213> ORGANISM: ARTIFICIAL SEQUENCE
<220> FEATURE:
<223> OTHER INFORMATION: Artificially synthesized forward primer

<400> SEQUENCE: 121
tggttaaact gtagtacatc catgga                                   26

<210> SEQ ID NO 122
<211> LENGTH: 21
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 122
accttttggg actggctttc t                                        21

<210> SEQ ID NO 123
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 123
tccacatgtc aggtgtctgc                                          20

<210> SEQ ID NO 124
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 124
gagatggggt ttcaccgtgt                                          20

<210> SEQ ID NO 125

```
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 125
ctaggctcct acaatgtgcc                                               20

<210> SEQ ID NO 126
<211> LENGTH: 16
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 126
gccgaggtgg gtggat                                                   16

<210> SEQ ID NO 127
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 127
gagtcgaaat ctctggggcc                                               20

<210> SEQ ID NO 128
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 128
ggacacccca tatcgcagag                                               20

<210> SEQ ID NO 129
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 129
ccgatgctgc tgaggataaa                                               20

<210> SEQ ID NO 130
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 130
tccagtgtgc aaagactctg                                               20

<210> SEQ ID NO 131
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 131
```
tggccccaaa ccctaaattt                                                         20

<210> SEQ ID NO 132
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 132
ccgtagaagc aaaggtagca                                                         20

<210> SEQ ID NO 133
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 133
ccttgcccct cttctgttgt                                                         20

<210> SEQ ID NO 134
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 134
cccacttgga gcctcagttt                                                         20

<210> SEQ ID NO 135
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 135 tgttgcccttcttctccaag                                                          20

<210> SEQ ID NO 136
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 136
aggtcttgtg gttcagaacg                                                         20

<210> SEQ ID NO 137
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 137
aatggtccca ctggaaatgg                                                         20

<210> SEQ ID NO 138
<211> LENGTH: 20
<212> TYPE: DNA

```
<213> ORGANISM: ARTIFICIAL SEQUENCE
<220> FEATURE:
<223> OTHER INFORMATION: Artificially synthesized reverse primer

<400> SEQUENCE: 138
ttagggaaca gcactttggg                                              20

<210> SEQ ID NO 139
<211> LENGTH: 20
<212> TYPE: DNA
<213> ORGANISM: ARTIFICIAL SEQUENCE
<220> FEATURE:
<223> OTHER INFORMATION: Artificially synthesized forward primer

<400> SEQUENCE: 139
catccaaagg tggcacttgc                                              20

<210> SEQ ID NO 140
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 140
acgttgcagc catacagaca                                              20

<210> SEQ ID NO 141
<211> LENGTH: 19
<212> TYPE: DNA
<213> ORGANISM: ARTIFICIAL SEQUENCE
<220> FEATURE:
<223> OTHER INFORMATION: Artificially synthesized forward primer

<400> SEQUENCE: 141
ttgtgcagcc atcacctct                                               19

<210> SEQ ID NO 142
<211> LENGTH: 20
<212> TYPE: DNA
<213> ORGANISM: ARTIFICIAL SEQUENCE
<220> FEATURE:
<223> OTHER INFORMATION: Artificially synthesized reverse primer

<400> SEQUENCE: 142
aaatcagatt aatggttgct                                              20
```